US009839669B2

(12) United States Patent
Lentzen et al.

(10) Patent No.: US 9,839,669 B2
(45) Date of Patent: Dec. 12, 2017

(54) ANTIVIRAL AGENT COMPRISING RECOMBINANT MISTLETOE LECTINS

(71) Applicant: Cytavis Biopharma GmbH, Hamburg (DE)

(72) Inventors: Hans Lentzen, Rosrath (DE); Klaus Witthohn, Overath (DE)

(73) Assignee: Cytavis Biopharma GmbH, Hamburg (DE)

( * ) Notice: Subject to any disclaimer, the term of this patent is extended or adjusted under 35 U.S.C. 154(b) by 0 days.

(21) Appl. No.: 15/064,285

(22) Filed: Mar. 8, 2016

(65) Prior Publication Data

US 2016/0175390 A1 Jun. 23, 2016

Related U.S. Application Data

(63) Continuation of application No. 13/983,101, filed as application No. PCT/EP2012/051708 on Feb. 1, 2012, now abandoned.

(30) Foreign Application Priority Data

Feb. 1, 2011 (DE) ........................ 10 2011 003 478

(51) Int. Cl.
| | | |
|---|---|---|
| A61K 38/00 | (2006.01) | |
| A61K 45/06 | (2006.01) | |
| C07K 14/42 | (2006.01) | |
| A61K 38/16 | (2006.01) | |

(52) U.S. Cl.
CPC ............ *A61K 38/168* (2013.01); *A61K 45/06* (2013.01); *C07K 14/42* (2013.01)

(58) Field of Classification Search
CPC ....... A61K 38/168; A61K 45/06; C07K 14/42
USPC ......................................................... 514/4.2
See application file for complete search history.

(56) References Cited

U.S. PATENT DOCUMENTS

| | | |
|---|---|---|
| 6,271,368 B1 | 8/2001 | Lentzen et al. |
| 6,531,125 B1 | 3/2003 | Borgford |
| 6,927,207 B1 | 8/2005 | Morris et al. |
| 2002/0045208 A1 | 4/2002 | Eck et al. |
| 2011/0217283 A1 | 9/2011 | Gloger et al. |

FOREIGN PATENT DOCUMENTS

| | | |
|---|---|---|
| DE | 19804210 A1 | 8/1999 |
| DE | 10149030 A1 | 4/2003 |
| EP | 0751221 A1 | 1/1997 |
| EP | 1012256 A2 | 6/2000 |

OTHER PUBLICATIONS

Park et al, "cDNA Cloning and Sequence Analysis of the Lectin Genes of the Korean Mistletoe (*Viscum album coloratum*)," Molecules and Cells, 2001, 12(2): 215-220.*
Hepatitis A from MayoClinic.com, pp. 1-2, Accessed Aug. 9, 2012.
Types of Viral Disorders from Merck manual, pp. 1-6, Accessed Apr. 4, 2015.
Dengue from Merck manual, pp. 1-3, Accessed Apr. 4, 2015.
Yellow fever from Merck manual, pp. 1-2, Accessed Apr. 4, 2015.
Acute Viral Hepatitis from Merck manual, pp. 1-8, Accessed Apr. 4, 2015.
Herpes Simplex Virus (HSV) Infections from Merck manual, pp. 1-3, Accessed Apr. 4, 2015.
Lavelle, E.C. et al., "Mistletoe Lectins Enhance Immune Responses to Intranasally Co-Administered Herpes Simplex Virus Glycoprotein D2," *Immunology*, vol. 107, pp. 268-274 (2002).
Karagoz, A. et al., "Antiviral Potency of Mistletoe (*Viscum album* ssp. *album*) Extracts against Human Parainfluenza Virus Type 2 in Vera Cells," *Phytotherapy Research*, vol. 17, pp. 560-562 (2003).
Stirpe, F. et al., "Ribosome-Inactivating Proteins: Progress and Problems," *Cell. Mol. Life Sci.*, vol. 63, pp. 1850-1866 (2006).
Song, S.K. et al., "Intranasal Immunization with Influenza Virus and Korean Mistletoe lectin C (KML-C) Induces Heterosubtypic Immunity in Mice," *Vaccine*, vol. 25, pp. 6359-6366 (2007).

* cited by examiner

*Primary Examiner* — Julie Ha
(74) *Attorney, Agent, or Firm* — Drinker Biddle & Reath LLP

(57) ABSTRACT

An antiviral agent containing recombinant mistletoe lectins for treating virus infections and a medicament and/or pharmaceutical composition for treating virus infections are described. Recombinant mistletoe lectin polypeptides can be a mistletoe lectin A-chain, as well as parts or fragments of the mistletoe lectin A-chain. The antiviral agent can be used for any number of virus infections, such as Herpes simplex, adenovirus, poliovirus, and poxvirus. Also, the antiviral agent can be used for skin virus warts, anogenital warts, mucous membrane warts and malignant tumors such as cervical cancer, penis and vulvar cancer.

8 Claims, No Drawings

SEQUENCE LISTING

<160> NUMBER OF SEQ ID NOS: 12

<210> SEQ ID NO 1
<211> LENGTH: 253
<212> TYPE: PRT
<213> ORGANISM: Artificial
<220> FEATURE:
<223> OTHER INFORMATION: EP0751221 recombinant Protein
<220> FEATURE:
<221> NAME/KEY: misc_feature
<222> LOCATION: (1)..(1)
<223> OTHER INFORMATION: Xaa can be Met or can be deleted
<220> FEATURE:
<221> NAME/KEY: misc_feature
<222> LOCATION: (5)..(5)
<223> OTHER INFORMATION: Xaa can be Ile or Leu
<220> FEATURE:
<221> NAME/KEY: misc_feature
<222> LOCATION: (16)..(16)
<223> OTHER INFORMATION: Xaa can be Glu or Asp

<400> SEQUENCE: 1

```
Xaa Tyr Glu Arg Xaa Arg Leu Arg Val Thr His Gln Thr Thr Gly Xaa
 1               5                  10                  15

Glu Tyr Phe Arg Phe Ile Thr Leu Leu Arg Asp Tyr Val Ser Ser Gly
             20                  25                  30

Ser Phe Ser Asn Glu Ile Pro Leu Leu Arg Gln Ser Thr Ile Pro Val
         35                  40                  45

Ser Asp Ala Gln Arg Phe Val Leu Val Glu Leu Thr Asn Gln Gly Gly
 50                  55                  60

Asp Ser Ile Thr Ala Ala Ile Asp Val Thr Asn Leu Tyr Val Val Ala
 65                  70                  75                  80

Tyr Gln Ala Gly Asp Gln Ser Tyr Phe Leu Arg Asp Ala Pro Arg Gly
             85                  90                  95

Ala Glu Thr His Leu Phe Thr Gly Thr Thr Arg Ser Ser Leu Pro Phe
            100                 105                 110

Asn Gly Ser Tyr Pro Asp Leu Glu Arg Tyr Ala Gly His Arg Asp Gln
        115                 120                 125

Ile Pro Leu Gly Ile Asp Gln Leu Ile Gln Ser Val Thr Ala Leu Arg
130                 135                 140

Phe Pro Gly Gly Ser Thr Arg Thr Gln Ala Arg Ser Ile Leu Ile Leu
145                 150                 155                 160

Ile Gln Met Ile Ser Glu Ala Ala Arg Phe Asn Pro Ile Leu Trp Arg
                165                 170                 175

Ala Arg Gln Tyr Ile Asn Ser Gly Ala Ser Phe Leu Pro Asp Val Tyr
            180                 185                 190

Met Leu Glu Leu Glu Thr Ser Trp Gly Gln Gln Ser Thr Gln Val Gln
        195                 200                 205

His Ser Thr Asp Gly Val Phe Asn Asn Pro Ile Arg Leu Ala Ile Pro
    210                 215                 220

Pro Gly Asn Phe Val Thr Leu Thr Asn Val Arg Asp Val Ile Ala Ser
225                 230                 235                 240

Leu Ala Ile Met Leu Phe Val Cys Gly Glu Arg Pro Ser
                245                 250
```

<210> SEQ ID NO 2
<211> LENGTH: 256
<212> TYPE: PRT
<213> ORGANISM: Artificial
<220> FEATURE:
<223> OTHER INFORMATION: EP1051495 recombinant Protein

```
<220> FEATURE:
<221> NAME/KEY: misc_feature
<222> LOCATION: (1)..(1)
<223> OTHER INFORMATION: Xaa can be Met or can be deleted
<220> FEATURE:
<221> NAME/KEY: misc_feature
<222> LOCATION: (16)..(16)
<223> OTHER INFORMATION: Xaa can be Asp or Glu
<220> FEATURE:
<221> NAME/KEY: misc_feature
<222> LOCATION: (64)..(64)
<223> OTHER INFORMATION: Xaa can be Gly or Gln
<220> FEATURE:
<221> NAME/KEY: misc_feature
<222> LOCATION: (67)..(67)
<223> OTHER INFORMATION: Xaa can be Ile or Val
<220> FEATURE:
<221> NAME/KEY: misc_feature
<222> LOCATION: (76)..(76)
<223> OTHER INFORMATION: Xaa can be Leu or Ala
<220> FEATURE:
<221> NAME/KEY: misc_feature
<222> LOCATION: (108)..(108)
<223> OTHER INFORMATION: Xaa can be Asp-Arg or can be deleted
<220> FEATURE:
<221> NAME/KEY: misc_feature
<222> LOCATION: (114)..(114)
<223> OTHER INFORMATION: Xaa can be Asn or Thr
<220> FEATURE:
<221> NAME/KEY: misc_feature
<222> LOCATION: (118)..(118)
<223> OTHER INFORMATION: Xaa can be Pro or Thr
<220> FEATURE:
<221> NAME/KEY: misc_feature
<222> LOCATION: (135)..(135)
<223> OTHER INFORMATION: Xaa can be Asp or Glu
<220> FEATURE:
<221> NAME/KEY: misc_feature
<222> LOCATION: (142)..(142)
<223> OTHER INFORMATION: Xaa can be Ser or Thr
<220> FEATURE:
<221> NAME/KEY: misc_feature
<222> LOCATION: (146)..(146)
<223> OTHER INFORMATION: Xaa can be Phe or Tyr
<220> FEATURE:
<221> NAME/KEY: misc_feature
<222> LOCATION: (153)..(153)
<223> OTHER INFORMATION: Xaa can be Ala or Thr
<220> FEATURE:
<221> NAME/KEY: misc_feature
<222> LOCATION: (178)..(178)
<223> OTHER INFORMATION: Xaa can be Ala or Tyr
<220> FEATURE:
<221> NAME/KEY: misc_feature
<222> LOCATION: (181)..(181)
<223> OTHER INFORMATION: Xaa can be Tyr or Asp
<220> FEATURE:
<221> NAME/KEY: misc_feature
<222> LOCATION: (186)..(186)
<223> OTHER INFORMATION: Xaa can be Ala or Glu
<220> FEATURE:
<221> NAME/KEY: misc_feature
<222> LOCATION: (192)..(192)
<223> OTHER INFORMATION: Xaa can be Val or Met
<220> FEATURE:
<221> NAME/KEY: misc_feature
<222> LOCATION: (220)..(220)
<223> OTHER INFORMATION: Xaa can be Ile or Phe
<220> FEATURE:
<221> NAME/KEY: misc_feature
<222> LOCATION: (225)..(226)
<223> OTHER INFORMATION: Xaa can be Pro-Ser or Pro-Thr
<220> FEATURE:
<221> NAME/KEY: misc_feature
<222> LOCATION: (233)..(233)
<223> OTHER INFORMATION: Xaa can be Thr or Ser
<220> FEATURE:
<221> NAME/KEY: misc_feature
<222> LOCATION: (237)..(237)
```

<223> OTHER INFORMATION: Xaa can be Asp or Ser
<220> FEATURE:
<221> NAME/KEY: misc_feature
<222> LOCATION: (255)..(256)
<223> OTHER INFORMATION: Xaa can be Ser-Ser or can be deleted

<400> SEQUENCE: 2

```
Xaa Tyr Glu Arg Leu Arg Leu Arg Val Thr His Gln Thr Thr Gly Xaa
1               5                   10                  15

Glu Tyr Phe Arg Phe Ile Thr Leu Leu Arg Asp Tyr Val Ser Ser Gly
            20                  25                  30

Ser Phe Ser Asn Glu Ile Pro Leu Leu Arg Gln Ser Thr Ile Pro Val
        35                  40                  45

Ser Asp Ala Gln Arg Phe Val Leu Val Glu Leu Thr Asn Gln Gly Xaa
    50                  55                  60

Asp Ser Xaa Thr Ala Ala Ile Asp Val Thr Asn Xaa Tyr Val Val Ala
65                  70                  75                  80

Tyr Gln Ala Gly Asp Gln Ser Tyr Phe Leu Arg Asp Ala Pro Arg Gly
                85                  90                  95

Ala Glu Thr His Leu Phe Thr Gly Thr Thr Arg Xaa Ser Ser Leu Pro
            100                 105                 110

Phe Xaa Gly Ser Tyr Xaa Asp Leu Glu Arg Tyr Ala Gly His Arg Asp
        115                 120                 125

Gln Ile Pro Leu Gly Ile Xaa Gln Leu Ile Gln Ser Val Xaa Ala Leu
    130                 135                 140

Arg Xaa Pro Gly Gly Ser Thr Arg Xaa Gln Ala Arg Ser Ile Leu Ile
145                 150                 155                 160

Leu Ile Gln Met Ile Ser Glu Ala Ala Arg Phe Asn Pro Ile Leu Trp
                165                 170                 175

Arg Xaa Arg Gln Xaa Ile Asn Ser Gly Xaa Ser Phe Leu Pro Asp Xaa
            180                 185                 190

Tyr Met Leu Glu Leu Glu Thr Ser Trp Gly Gln Gln Ser Thr Gln Val
        195                 200                 205

Gln His Ser Thr Asp Gly Val Phe Asn Asn Pro Xaa Arg Leu Ala Ile
    210                 215                 220

Xaa Xaa Gly Asn Phe Val Thr Leu Xaa Asn Val Arg Xaa Val Ile Ala
225                 230                 235                 240

Ser Leu Ala Ile Met Leu Phe Val Cys Gly Glu Arg Pro Ser Xaa Xaa
                245                 250                 255
```

<210> SEQ ID NO 3
<211> LENGTH: 257
<212> TYPE: PRT
<213> ORGANISM: Artificial
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 3

```
Xaa Tyr Glu Arg Leu Arg Leu Arg Val Thr His Gln Thr Thr Gly Asp
1               5                   10                  15

Glu Tyr Phe Arg Phe Ile Thr Leu Leu Arg Asp Tyr Val Ser Ser Gly
            20                  25                  30

Ser Phe Ser Asn Glu Ile Pro Leu Leu Arg Gln Ser Thr Ile Pro Val
        35                  40                  45
```

-continued

```
Ser Asp Ala Gln Arg Phe Val Leu Val Glu Leu Thr Asn Gln Gly Gln
     50                  55                  60

Asp Ser Ile Thr Ala Ala Ile Asp Val Thr Asn Ala Tyr Val Val Ala
 65                  70                  75                  80

Tyr Gln Ala Gly Asp Gln Ser Tyr Phe Leu Arg Asp Ala Pro Arg Gly
                 85                  90                  95

Ala Glu Thr His Leu Phe Thr Gly Thr Arg Asp Arg Ser Ser Leu
                100                 105                 110

Pro Phe Thr Gly Ser Tyr Thr Asp Leu Glu Arg Tyr Ala Gly His Arg
                115                 120                 125

Asp Gln Ile Pro Leu Gly Ile Glu Gln Leu Ile Gln Ser Val Ser Ala
    130                 135                 140

Leu Arg Tyr Pro Gly Gly Ser Thr Arg Ala Gln Ala Arg Ser Ile Leu
145                 150                 155                 160

Ile Leu Ile Gln Met Ile Ser Glu Ala Ala Arg Phe Asn Pro Ile Leu
                165                 170                 175

Trp Arg Tyr Arg Gln Asp Ile Asn Ser Gly Glu Ser Phe Leu Pro Asp
                180                 185                 190

Met Tyr Met Leu Glu Leu Glu Thr Ser Trp Gly Gln Gln Ser Thr Gln
                195                 200                 205

Val Gln His Ser Thr Asp Gly Val Phe Asn Asn Pro Phe Arg Leu Ala
    210                 215                 220

Ile Ser Thr Gly Asn Phe Val Thr Leu Ser Asn Val Arg Ser Val Ile
225                 230                 235                 240

Ala Ser Leu Ala Ile Met Leu Phe Val Cys Gly Glu Arg Pro Ser Ser
                245                 250                 255

Ser
```

<210> SEQ ID NO 4
<211> LENGTH: 264
<212> TYPE: PRT
<213> ORGANISM: Artificial
<220> FEATURE:
<223> OTHER INFORMATION: EP0751221 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 4

```
Xaa Asp Asp Val Thr Cys Ser Ala Ser Glu Pro Thr Val Arg Ile Val
 1               5                  10                  15

Gly Arg Asn Gly Met Cys Val Asp Val Arg Asp Asp Asp Phe Arg Asp
                 20                  25                  30

Gly Asn Gln Ile Gln Leu Trp Pro Ser Lys Ser Asn Asn Asp Pro Asn
             35                  40                  45

Gln Leu Trp Thr Ile Lys Arg Asp Gly Thr Ile Arg Ser Asn Gly Ser
    50                  55                  60

Cys Leu Thr Thr Tyr Gly Tyr Thr Ala Gly Val Tyr Val Met Ile Phe
 65                  70                  75                  80

Asp Cys Asn Thr Ala Val Arg Glu Ala Thr Leu Trp Gln Ile Trp Gly
                 85                  90                  95

Asn Gly Thr Ile Ile Asn Pro Arg Ser Asn Leu Val Leu Ala Ala Ser
                100                 105                 110

Ser Gly Ile Lys Gly Thr Thr Leu Thr Val Gln Thr Leu Asp Tyr Thr
                115                 120                 125
```

```
Leu Gly Gln Gly Trp Leu Ala Gly Asn Asp Thr Ala Pro Arg Glu Val
        130                 135                 140

Thr Ile Tyr Gly Phe Arg Asp Leu Cys Met Glu Ser Asn Gly Gly Ser
145                 150                 155                 160

Val Trp Val Glu Thr Cys Val Ser Ser Gln Lys Asn Gln Arg Trp Ala
                165                 170                 175

Leu Tyr Gly Asp Gly Ser Ile Arg Pro Lys Gln Asn Gln Asp Gln Cys
                180                 185                 190

Leu Thr Cys Gly Arg Asp Ser Val Ser Thr Val Ile Asn Ile Val Ser
            195                 200                 205

Cys Ser Ala Gly Ser Ser Gly Gln Arg Trp Val Phe Thr Asn Glu Gly
210                 215                 220

Ala Ile Leu Asn Leu Lys Asn Gly Leu Ala Met Asp Val Ala Gln Ala
225                 230                 235                 240

Asn Pro Lys Leu Arg Arg Ile Ile Ile Tyr Pro Ala Thr Gly Lys Pro
                245                 250                 255

Asn Gln Met Trp Leu Pro Val Pro
            260
```

```
<210> SEQ ID NO 5
<211> LENGTH: 268
<212> TYPE: PRT
<213> ORGANISM: Artificial
<220> FEATURE:
<223> OTHER INFORMATION: EP0751221 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 5
```

```
Xaa Asp Asp Val Thr Cys Ser Ala Ser Glu Pro Thr Val Arg Ile Val
1               5                   10                  15

Gly Arg Asn Gly Met Cys Val Asp Val Arg Asp Asp Phe Arg Asp
                20                  25                  30

Gly Asn Gln Ile Gln Leu Trp Pro Ser Lys Ser Asn Asn Asp Pro Asn
            35                  40                  45

Gln Leu Trp Thr Ile Lys Arg Asp Gly Thr Ile Arg Ser Asn Gly Ser
    50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Leu Trp Gln Ile Trp Gly
                85                  90                  95

Asn Gly Thr Ile Ile Asn Pro Arg Ser Asn Leu Val Leu Ala Ala Ser
                100                 105                 110

Ser Gly Ile Lys Gly Thr Thr Leu Thr Val Gln Thr Leu Asp Tyr Thr
            115                 120                 125

Leu Gly Gln Gly Trp Leu Ala Gly Asn Asp Thr Ala Pro Arg Glu Val
        130                 135                 140

Thr Ile Tyr Gly Phe Arg Asp Leu Cys Met Glu Ser Asn Gly Gly Ser
145                 150                 155                 160

Val Trp Val Glu Thr Cys Val Ser Ser Gln Lys Asn Gln Arg Trp Ala
                165                 170                 175

Leu Tyr Gly Asp Gly Ser Ile Arg Pro Lys Gln Asn Gln Asp Gln Cys
                180                 185                 190

Leu Thr Cys Gly Arg Asp Ser Val Ser Thr Val Ile Asn Ile Val Ser
            195                 200                 205
```

```
Cys Ser Ala Gly Ser Ser Gly Gln Arg Trp Val Phe Thr Asn Glu Gly
        210                 215                 220

Ala Ile Leu Asn Leu Lys Asn Gly Leu Ala Met Asp Val Ala Gln Ala
225                 230                 235                 240

Asn Pro Lys Leu Arg Arg Ile Ile Ile Tyr Pro Ala Thr Gly Lys Pro
                245                 250                 255

Asn Gln Met Trp Leu Pro Val Pro Gly Gly Tyr His
                260                 265

<210> SEQ ID NO 6
<211> LENGTH: 265
<212> TYPE: PRT
<213> ORGANISM: Artificial
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted
<220> FEATURE:
<221> NAME/KEY: misc_feature
<222> LOCATION: (19)..(19)
<223> OTHER INFORMATION: Xaa can be Asn or Ser
<220> FEATURE:
<221> NAME/KEY: misc_feature
<222> LOCATION: (22)..(22)
<223> OTHER INFORMATION: Xaa can be Cys or Arg
<220> FEATURE:
<221> NAME/KEY: misc_feature
<222> LOCATION: (57)..(57)
<223> OTHER INFORMATION: Xaa can be Gly or Asn
<220> FEATURE:
<221> NAME/KEY: misc_feature
<222> LOCATION: (96)..(96)
<223> OTHER INFORMATION: Xaa can be Gly or Asn
<220> FEATURE:
<221> NAME/KEY: misc_feature
<222> LOCATION: (158)..(158)
<223> OTHER INFORMATION: Xaa can be Gly or Gln
<220> FEATURE:
<221> NAME/KEY: misc_feature
<222> LOCATION: (167)..(167)
<223> OTHER INFORMATION: Xaa can be Val or Asp
<220> FEATURE:
<221> NAME/KEY: misc_feature
<222> LOCATION: (171)..(171)
<223> OTHER INFORMATION: Xaa can be Gln or Lys
<220> FEATURE:
<221> NAME/KEY: misc_feature
<222> LOCATION: (174)..(175)
<223> OTHER INFORMATION: Xaa can be Gly or can be deleted or can be
    Gly-Arg or Gly-Lys or Arg or Lys
<220> FEATURE:
<221> NAME/KEY: misc_feature
<222> LOCATION: (196)..(196)
<223> OTHER INFORMATION: Xaa can be Cys or Val or Ser
<220> FEATURE:
<221> NAME/KEY: misc_feature
<222> LOCATION: (212)..(213)
<223> OTHER INFORMATION: Xaa can be Ala-Ala or Ala-Gly or Gly-Ala or
    Gly-Gly
<220> FEATURE:
<221> NAME/KEY: misc_feature
<222> LOCATION: (215)..(216)
<223> OTHER INFORMATION: Xaa can be Ser-Ser or Ser-Gly or Gly-Ser or
    Gly-Gly
<220> FEATURE:
<221> NAME/KEY: misc_feature
<222> LOCATION: (225)..(225)
<223> OTHER INFORMATION: Xaa can be Gly or Tyr
<220> FEATURE:
<221> NAME/KEY: misc_feature
<222> LOCATION: (232)..(236)
<223> OTHER INFORMATION: Xaa232 can be Asn, Ser, Thr or Lys, Xaa233 can
```

-continued be Ser or Gly, Xaa234 can be Leu or Pro, Xaa235 can be Ala or Met,
Xaa 236 can be Met or Val
<220> FEATURE:
<221> NAME/KEY: misc_feature
<222> LOCATION: (265)..(265)
<223> OTHER INFORMATION: Xaa can be Pro or Phe

<400> SEQUENCE: 6

Xaa Asp Asp Val Thr Cys Ser Ala Ser Glu Pro Thr Val Arg Ile Val
1               5                   10                  15

Gly Arg Xaa Gly Met Xaa Val Asp Val Arg Asp Asp Phe His Asp
            20                  25                  30

Gly Asn Gln Ile Gln Leu Trp Pro Ser Lys Ser Asn Asn Asp Pro Asn
            35                  40                  45

Gln Leu Trp Thr Ile Lys Arg Asp Xaa Thr Ile Arg Ser Asn Gly Ser
    50                  55                  60

Cys Leu Thr Thr Tyr Gly Tyr Thr Ala Gly Val Tyr Val Met Ile Phe
65              70                  75                  80

Asp Cys Asn Thr Ala Val Arg Glu Ala Thr Ile Trp Gln Ile Trp Xaa
                85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
            115                 120                 125

Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Xaa Gly Ser
145                 150                 155                 160

Val Trp Val Glu Thr Cys Xaa Ser Ser Gln Xaa Asn Gln Xaa Xaa Trp
                165                 170                 175

Ala Leu Tyr Gly Asp Gly Ser Ile Arg Pro Lys Gln Asn Gln Asp Gln
            180                 185                 190

Cys Leu Thr Xaa Gly Arg Asp Ser Val Ser Thr Val Ile Asn Ile Val
            195                 200                 205

Ser Cys Ser Xaa Xaa Ser Xaa Xaa Gln Arg Trp Val Phe Thr Asn Glu
            210                 215                 220

Xaa Ala Ile Leu Asn Leu Lys Xaa Xaa Xaa Xaa Xaa Asp Val Ala Gln
225                 230                 235                 240

Ala Asn Pro Lys Leu Arg Arg Ile Ile Ile Tyr Pro Ala Thr Gly Lys
            245                 250                 255

Pro Asn Gln Met Trp Leu Pro Val Xaa
            260                 265

<210> SEQ ID NO 7
<211> LENGTH: 264
<212> TYPE: PRT
<213> ORGANISM: Artificial
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 7

Xaa Asp Asp Val Thr Cys Ser Ala Ser Glu Pro Thr Val Arg Ile Val
1               5                   10                  15

Gly Arg Asn Gly Met Cys Val Asp Val Arg Asp Asp Phe His Asp
            20                  25                  30

Gly Asn Gln Ile Gln Leu Trp Pro Ser Lys Ser Asn Asn Asp Pro Asn
            35                  40                  45

Gln Leu Trp Thr Ile Lys Arg Asp Gly Thr Ile Arg Ser Asn Gly Ser
    50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Gly
                85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
            115                 120                 125

Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Gly Gly Ser
145                 150                 155                 160

Val Trp Val Glu Thr Cys Val Ser Ser Gln Gln Asn Gln Arg Trp Ala
                165                 170                 175

Leu Tyr Gly Asp Gly Ser Ile Arg Pro Lys Gln Asn Gln Asp Gln Cys
            180                 185                 190

Leu Thr Cys Gly Arg Asp Ser Val Ser Thr Val Ile Asn Ile Val Ser
            195                 200                 205

Cys Ser Ala Gly Ser Ser Gly Gln Arg Trp Val Phe Thr Asn Glu Gly
210                 215                 220

Ala Ile Leu Asn Leu Lys Asn Gly Leu Ala Met Asp Val Ala Gln Ala
225                 230                 235                 240

Asn Pro Lys Leu Arg Arg Ile Ile Ile Tyr Pro Ala Thr Gly Lys Pro
                245                 250                 255

Asn Gln Met Trp Leu Pro Val Pro
            260

<210> SEQ ID NO 8
<211> LENGTH: 265
<212> TYPE: PRT
<213> ORGANISM: Artificial
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 8

Xaa Asp Asp Val Thr Cys Ser Ala Ser Glu Pro Thr Val Arg Ile Val
1               5                   10                  15

Gly Arg Asn Gly Met Arg Val Asp Val Arg Asp Asp Asp Phe His Asp
            20                  25                  30

Gly Asn Gln Ile Gln Leu Trp Pro Ser Lys Ser Asn Asn Asp Pro Asn
            35                  40                  45

Gln Leu Trp Thr Ile Lys Arg Asp Gly Thr Ile Arg Ser Asn Gly Ser
    50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Asp
                85                  90                  95

Asn Gly Thr Ile Ile Asn Pro Arg Ser Asn Leu Val Leu Ala Ala Ser

```
                  100                 105                 110
Ser Gly Ile Lys Gly Thr Thr Leu Thr Val Gln Thr Leu Asp Tyr Thr
            115                 120                 125

Leu Gly Gln Gly Trp Leu Ala Gly Asn Asp Thr Ala Pro Arg Glu Val
        130                 135                 140

Thr Ile Tyr Gly Phe Arg Asp Leu Cys Met Glu Ser Asn Gly Gly Ser
145                 150                 155                 160

Val Trp Val Glu Thr Cys Asp Ser Ser Gln Lys Asn Gln Gly Lys Trp
                165                 170                 175

Ala Leu Tyr Gly Asp Gly Ser Ile Arg Pro Lys Gln Asn Gln Asp Gln
            180                 185                 190

Cys Leu Thr Ser Gly Arg Asp Ser Val Ser Thr Val Ile Asn Ile Val
        195                 200                 205

Ser Cys Ser Gly Ala Ser Gly Ser Gln Arg Trp Val Phe Thr Asn Glu
    210                 215                 220

Gly Ala Ile Leu Asn Leu Lys Asn Gly Leu Ala Met Asp Val Ala Gln
225                 230                 235                 240

Ala Asn Pro Lys Leu Arg Arg Ile Ile Ile Tyr Pro Ala Thr Gly Lys
                245                 250                 255

Pro Asn Gln Met Trp Leu Pro Val Phe
            260                 265

<210> SEQ ID NO 9
<211> LENGTH: 265
<212> TYPE: PRT
<213> ORGANISM: Artificial
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 9

Xaa Asp Asp Val Thr Cys Ser Ala Ser Glu Pro Thr Val Arg Ile Val
1               5                   10                  15

Gly Arg Ser Gly Met Arg Val Asp Val Arg Asp Asp Phe His Asp
            20                  25                  30

Gly Asn Gln Ile Gln Leu Trp Pro Ser Lys Ser Asn Asn Asp Pro Asn
        35                  40                  45

Gln Leu Trp Thr Ile Lys Arg Asp Asn Thr Ile Arg Ser Asn Gly Ser
    50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Asp
                85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
        115                 120                 125

Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Gly Gly Ser
145                 150                 155                 160

Val Trp Val Glu Thr Cys Asp Ser Ser Gln Lys Asn Gln Gly Lys Trp
                165                 170                 175
```

```
Ala Leu Tyr Gly Asp Gly Ser Ile Arg Pro Lys Gln Asn Gln Asp Gln
            180                 185                 190

Cys Leu Thr Val Gly Arg Asp Ser Val Ser Thr Val Ile Asn Ile Val
        195                 200                 205

Ser Cys Ser Gly Ala Ser Gly Ser Gln Arg Trp Val Phe Thr Asn Glu
    210                 215                 220

Tyr Ala Ile Leu Asn Leu Lys Ser Gly Leu Ala Met Asp Val Ala Gln
225                 230                 235                 240

Ala Asn Pro Lys Leu Arg Arg Ile Ile Ile Tyr Pro Ala Thr Gly Lys
            245                 250                 255

Pro Asn Gln Met Trp Leu Pro Val Phe
        260                 265

<210> SEQ ID NO 10
<211> LENGTH: 265
<212> TYPE: PRT
<213> ORGANISM: Artificial
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 10

Xaa Asp Asp Val Thr Cys Ser Ala Ser Glu Pro Thr Val Arg Ile Val
1               5                   10                  15

Gly Arg Asn Gly Met Arg Val Asp Val Arg Asp Asp Asp Phe His Asp
            20                  25                  30

Gly Asn Gln Ile Gln Leu Trp Pro Ser Lys Ser Asn Asn Asp Pro Asn
        35                  40                  45

Gln Leu Trp Thr Ile Lys Arg Asp Gly Thr Ile Arg Ser Asn Gly Ser
    50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Asp
                85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
        115                 120                 125

Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Gly Gly Ser
145                 150                 155                 160

Val Trp Val Glu Thr Cys Asp Ser Ser Gln Lys Asn Gln Gly Lys Trp
                165                 170                 175

Ala Leu Tyr Gly Asp Gly Ser Ile Arg Pro Lys Gln Asn Gln Asp Gln
            180                 185                 190

Cys Leu Thr Ser Gly Arg Asp Ser Val Ser Thr Val Ile Asn Ile Val
        195                 200                 205

Ser Cys Ser Gly Ala Ser Gly Ser Gln Arg Trp Val Phe Thr Asn Glu
    210                 215                 220

Gly Ala Ile Leu Asn Leu Lys Thr Gly Leu Ala Met Asp Val Ala Gln
225                 230                 235                 240

Ala Asn Pro Lys Leu Arg Arg Ile Ile Ile Tyr Pro Ala Thr Gly Lys
            245                 250                 255
```

```
Pro Asn Gln Met Trp Leu Pro Val Phe
            260                 265
```

<210> SEQ ID NO 11
<211> LENGTH: 265
<212> TYPE: PRT
<213> ORGANISM: Artificial
<220> FEATURE:
<223> OTHER INFORMATION: EP1051495 recombinant Protein
<220> FEATURE:
<221> NAME/KEY: misc_feature
<222> LOCATION: (1)..(1)
<223> OTHER INFORMATION: Xaa can be Met or can be deleted

<400> SEQUENCE: 11

```
Xaa Asp Asp Val Thr Cys Ser Ala Ser Glu Pro Thr Val Arg Ile Val
1               5                   10                  15

Gly Arg Asn Gly Met Arg Val Asp Val Arg Asp Asp Phe His Asp
            20                  25                  30

Gly Asn Gln Ile Gln Leu Trp Pro Ser Lys Ser Asn Asn Asp Pro Asn
            35                  40                  45

Gln Leu Trp Thr Ile Lys Arg Asp Gly Thr Ile Arg Ser Asn Gly Ser
50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Asp
                85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
            115                 120                 125

Leu Gly Gln Gly Trp Leu Ala Gly Asn Asp Thr Ala Pro Arg Glu Val
130                 135                 140

Thr Ile Tyr Gly Phe Arg Asp Leu Cys Met Glu Ser Asn Gly Gly Ser
145                 150                 155                 160

Val Trp Val Glu Thr Cys Asp Ser Ser Gln Lys Asn Gln Gly Lys Trp
                165                 170                 175

Ala Leu Tyr Gly Asp Gly Ser Ile Arg Pro Lys Gln Asn Gln Asp Gln
            180                 185                 190

Cys Leu Thr Ser Gly Arg Asp Ser Val Ser Thr Val Ile Asn Ile Val
            195                 200                 205

Ser Cys Ser Gly Ala Ser Gly Ser Gln Arg Trp Val Phe Thr Asn Glu
    210                 215                 220

Gly Ala Ile Leu Asn Leu Lys Lys Gly Pro Ala Met Asp Val Ala Gln
225                 230                 235                 240

Ala Asn Pro Lys Leu Arg Arg Ile Ile Ile Tyr Pro Ala Thr Gly Lys
                245                 250                 255

Pro Asn Gln Met Trp Leu Pro Val Phe
            260                 265
```

<210> SEQ ID NO 12
<211> LENGTH: 265
<212> TYPE: PRT
<213> ORGANISM: Artificial
<220> FEATURE:
<223> OTHER INFORMATION: EP1051495 recombinant Protein
<220> FEATURE:
<221> NAME/KEY: misc_feature
<222> LOCATION: (1)..(1)

-continued

<223> OTHER INFORMATION: Xaa can be Met or can be deleted

<400> SEQUENCE: 12

```
Xaa Asp Asp Val Thr Cys Ser Ala Ser Glu Pro Thr Val Arg Ile Val
1               5                   10                  15

Gly Arg Asn Gly Met Arg Val Asp Val Arg Asp Asp Phe His Asp
            20                  25                  30

Gly Asn Gln Ile Gln Leu Trp Pro Ser Lys Ser Asn Asn Asp Pro Asn
            35                  40                  45

Gln Leu Trp Thr Ile Lys Arg Asp Gly Thr Ile Arg Ser Asn Gly Ser
    50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Asp
                85                  90                  95

Asn Gly Thr Ile Ile Asn Pro Arg Ser Asn Leu Val Leu Ala Ala Ser
                100                 105                 110

Ser Gly Ile Lys Gly Thr Thr Leu Thr Val Gln Thr Leu Asp Tyr Thr
            115                 120                 125

Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Gly Gly Ser
145                 150                 155                 160

Val Trp Val Glu Thr Cys Asp Ser Ser Gln Lys Asn Gln Gly Lys Trp
                165                 170                 175

Ala Leu Tyr Gly Asp Gly Ser Ile Arg Pro Lys Gln Asn Gln Asp Gln
            180                 185                 190

Cys Leu Thr Ser Gly Arg Asp Ser Val Ser Thr Val Ile Asn Ile Val
            195                 200                 205

Ser Cys Ser Gly Ala Ser Gly Ser Gln Arg Trp Val Phe Thr Asn Glu
    210                 215                 220

Gly Ala Ile Leu Asn Leu Lys Asn Ser Leu Met Val Asp Val Ala Gln
225                 230                 235                 240

Ala Asn Pro Lys Leu Arg Arg Ile Ile Ile Tyr Pro Ala Thr Gly Lys
                245                 250                 255

Pro Asn Gln Met Trp Leu Pro Val Phe
                260                 265
```

ANTIVIRAL AGENT COMPRISING RECOMBINANT MISTLETOE LECTINS

CROSS-REFERENCE TO RELATED APPLICATIONS

The application is a continuation application of U.S. application Ser. No. 13/983,101, filed Nov. 14, 2013, the contents of which are incorporated herein by reference in their entirety. U.S. application Ser. No. 13/983,101 is the 371 National Stage of PCT/EP2012/051708, filed Feb. 1, 2012 which claims the benefit of priority of German application No. 10 2011 003 478.1, filed Feb. 1, 2011.

SEQUENCE LISTING

The instant application contains a Sequence Listing which has been submitted in ASCII format via EFS-Web and is hereby incorporated by reference in its entirety. Said ASCII copy, created on Mar. 8, 2016 is named 74062_0001_01_SL_ST25.txt and is 32,885 bytes in size.

The invention relates to an antiviral agent comprising recombinant mistletoe lectins for treating virus infections, and to a medicinal drug and/or a pharmaceutical composition for treating virus infections.

When virus infections occur, viruses penetrate the organism, where they replicate. The reaction of the organism that generally ensues can manifest itself in an infectious disease. A large number of diseases can be caused by viruses in humans. At present, preventive immunizations are only possible against a limited number of virus infections. Because viruses, contrary to bacteria, are not cells, they cannot be destroyed as bacteria can be. It is only possible to inhibit or prevent a viral infection and virus replication.

An infection with Herpes simplex viruses will be described hereafter by way of example for the large number of possible virus diseases.

Herpes simplex viruses are common worldwide and humans are the only natural host to them, serving as a reservoir. In Germany, antibodies against Herpes simplex viruses were detected in 84 to 92% of persons of an age-normalized random sample analysis. Diseases caused by the Herpes simplex virus are among the most frequent infectious diseases of the skin. The majority of infections occur on the face and in the genital region. It is commonly known that the Herpes simplex virus is a recurring virus infection, which is characterized by the appearance of individual or multiple accumulations of small vesicles on the skin or mucous membranes.

There are two primary types of the Herpes simplex virus (HSV)—HSV 1 and HSV 2. They differ slightly from each other in terms of their disease patterns and disease localizations. Clinically different HSV infections are distinguished according to the occurrence and localization of the disease symptoms, with the most important ones being Herpes simplex labialis (oral herpes) and Herpes simplex genitalis. After an initial infection, the virus will always remain in the organism in a dormant state (latency), which is referred to as a persistent infection. The treatment of HSV infections cannot end this persistence, but attempts to prevent the replication of the virus after reactivation from latency has occurred.

The treatment of virus infections includes the use of active ingredients, which are subsumed under the term 'virostatic agents'. These medicinal drugs intervene in the replication of viruses in various respects and thus prevent further spreading of the pathogen. The virostatic agents frequently employed for fighting Herpes simplex viruses in the case of oral herpes belong to the group known as nucleoside analogs. These inhibit DNA synthesis and consequently replication of the viruses. Because nucleoside analogs always intervene in virus replication, they work only with actively reproducing viruses. Among these nucleoside analogs, the compound known as Aciclovir has proven to be effective, however it also has some side effects. Aciclovir is eliminated via the kidneys. Renal problems were found with high dosages that were administered quickly and intravenously, because Aciclovir can then crystallize out in the kidneys. Aciclovir can also be incorporated into cellular DNA and thus constitutes a chromosome mutagen. Additionally, resistances may develop.

While nucleoside analogs are highly valuable, a need remains for improved medicinal drugs so as to be able to better treat the symptoms that occur by the outbreaks of virus infections.

Additionally, some viruses exist, which favor the development of cancer because they cause a latent infection over an extended period. For example, papilloma viruses have been linked to cervical cancer, and the Epstein-Barr virus to nasopharyngeal cancer.

Mistletoe extracts have been used therapeutically for centuries. Mistletoe preparations have been employed notably in cancer therapy with varying success (Bocci V 1993 J Biol Regulators and Homeostatic Agents 7(1): 1-6; Gabius H-J, Gabius S, Joshi S S et al. 1993 Planta Med 60: 2-7; Gabius H-J & Gabius S 1994 PZ 139: 9-16; Ganguly C & Das S 1994 Chemotherapy 40: 272-278, Hajto T, Hostanska K, Gabius H_J 1989 Cancer Res 49: 4803-4808, Hajto T, Hostanska K, Frei K et al. 1990 Cancer Res. 50: 3322-3326). It was found that the therapeutic effects are induced in particular by so-called mistletoe lectins (viscumin, Viscum album agglutinin, VAA). In addition to a cytotoxic effect, the mistletoe lectins reportedly also cause nonspecific immune stimulation, the positive effects of which are used for the treatment of tumor patients. Various analyses conducted with mistletoe lectins in vitro (Hajto et al., 1990 (supra); Mannel D N, Becker H, Gundt A et al. 1991 Cancer Immunol Immunother 33: 177-182; Beuth J, Ko K L, Tunggal L et al. 1993 Drug Res 43: 166-169) and in vivo (Hajto T 1986 Oncology 43 suppl 1: 51-65; Hajto et al., 1989 (supra), Beuth J, Ko H L, Gabius H-J et al. 1991 In Vivo 5: 29-32; Beuth J, Ko H L, Gabius H-J et al. 1992 J Clin Invest 70: 658-661) as well as clinical studies (Beuth et al., 1992 (supra)) showed an increased release of inflammatory cytokines (TNF-alpha, IL-1, IL-6) and an activation of cellular components of the immune system (Th cells, NK cells).

Only few studies have previously analyzed the antiviral effectiveness of native mistletoe lectins, which represent extracts from mistletoe lectins. Karagöz et al. (Phytother. Res. 17, 560-562, 2003) previously analyzed the antiviral effectiveness of extracts of European mistletoe (Viscum album L.). Karagöz et al explored whether different mistletoe extracts have an antiviral effectiveness for the human parainfluenza virus type 2 (HPIV-2). To this end, the following mistletoe extracts were analyzed: an aqueous extract, an ethanol extract, a petroleum ether extract, a chloroform extract and an acetone extract. The test system consisted of Vero cells, the human HPIV-2 and the different mistletoe extracts. Cytotoxicity tests and plaque assays were carried out. It was shown that the aqueous extract had a significant effect against the replication of HPIV-2, while the chloroform extract had moderate activity. The remaining extracts showed no significant effect on the replication of HPIV-2.

The mistletoe extracts described in the related art are multi-substance mixtures of plant origin, the ingredients of which are not described nor characterized. The analyses conducted by Karagöz et al. therefore do not clarify which substances in the aqueous extract exhibited the activity against HPIV-2 replication. The composition of the ingredients of plant extracts is heterogeneous. As a result, difficulties exist with adjusting extracts to particular concentrations of one or more ingredients in terms of a pharmacological effect.

Previously, three mistletoe lectins (ML-I, ML-II, ML-III) having different molecular weights and sugar-binding specificities were identified by way of analyses of the mistletoe extract. It was shown that the immune-stimulating effect of the mistletoe extract can be attributed to ML-I. The ML-I lectin has two glycosylated A- and B-chains (MLA and MLB). The A-chain is responsible for an enzymatic inactivation of ribosomes (Endo et al., 1988), while the B-chain is involved in carbohydrate binding. The two chains are linked to each other by disulfide bridges. The resulting mistletoe lectin monomers can join together to form dimers, forming non-covalent bonds.

It is now also possible to produce recombinant biologically active mistletoe lectin. EP 0 751 221 describes the preparation of mistletoe lectin polypeptides as a structurally homogeneous substance in pure form, wherein, starting from the gene sequences of the mistletoe lectin, recombinant, highly pure individual chains (A-chain, B-chain) are produced, which can be reassociated in vitro and thus result in a recombinant mistletoe lectin holoprotein, which is homogeneous in terms of its protein chemistry, enzymatic activity and structure, this being so-called Aviscumin. According to EP 0 751 221, the recombinant mistletoe lectin polypeptide is useful for therapeutic purposes both as a holoprotein, as a partial chain and in the form of subfragments and is covered by the invention.

Previously, recombinant mistletoe lectins were used in particular for the treatment of tumor diseases. While EP 0 751 221 mentions that recombinant mistletoe lectins can also conceivably be used for treating infectious diseases, no suggestions are disclosed that a treatment of virus infections with recombinant mistletoe lectins is effective.

It is the object of the present invention to provide antiviral agents, which can be used to effectively treat virus infections. Another object of the present invention is to provide a medicinal drug and pharmaceutical compositions for treating virus infections.

The object is achieved by the provision of an antiviral agent, as well as by the provision of a medicinal drug and a pharmaceutical composition, wherein these comprise recombinant mistletoe lectins for the treatment and prophylaxis of virus infections, wherein the recombinant mistletoe lectins comprise the amino acid sequences below.

The antiviral agent according to the invention preferably comprises the mistletoe lectin A-chain (MLA) and the mistletoe lectin B-chain (MLB), either individually or together, including in the form of dimers (see, for example, EP 0 751 221 or EP 1 051 495).

The recombinant mistletoe lectin polypeptide of the mistletoe lectin A-chain comprises the following sequences: SEQ ID Nos. 1-3, including the isoforms thereof or a functional fragment thereof.

The recombinant mistletoe lectin polypeptide of the mistletoe lectin B-chain comprises the following sequences: SEQ ID Nos. 4-12, including the isoforms thereof or a functional fragment thereof (hereafter collectively referred to as "recombinant mistletoe lectins").

Additionally, Aviscumin is preferred, a heterodimer composed of the sequences SEQ ID No. 1 and SEQ ID No. 4.

The invention relates to an antiviral agent comprising recombinant mistletoe lectin for use with virus infections or so as to prevent virus infections, wherein the recombinant mistletoe lectin is selected from the group of the amino acid sequences SEQ ID Nos. 1-12, or comprises parts and fragments thereof, or a combination thereof.

In the context of the present invention, the term "functional fragment" defines fragments of said polypeptides, which have the same biological function as the polypeptide implemented above with the respective amino acid sequence.

The term "same biological function" in this context describes, for example, that fragments or derivatives of the polypeptides induce the same signals in a cell as said peptides. Examples of fragments include peptide domains having defined functions. The "same biological function" also encompasses cytotoxicity, immune stimulation (both of the native and of the adaptive immune system), stimulation of the release of cytokines, antigenicity, induction of the expression or activation of surface markers, induction of apoptosis, or endorphin stimulation.

The expression "biological activity of the recombinant mistletoe lectin" shall be understood here to mean any biological activity from the spectrum of all the biological activities of the recombinant mistletoe lectin. For example, such a function is the pharmacological effect of the recombinant mistletoe lectin.

Analyses of ML-I monomers showed 25 different isoforms, which can be attributed to different combinations of various A- and B-chains as well as different glycosylation states of the chains.

The present invention therefore also relates to a mistletoe lectin polypeptide or a fragment thereof, which according to the invention comprises the sequence variability of the different MLA and MLB chains for the sequences SEQ ID Nos. 1-12.

The antiviral agent according to the invention preferably includes a recombinant mistletoe lectin polypeptide having the sequences SEQ ID Nos. 1-12, or a functional fragment thereof, or any arbitrary combination thereof.

As was already mentioned above, recombinant mistletoe lectins previously were used primarily for the treatment of tumor diseases. However, to this day, it has not been shown that recombinant mistletoe lectins have an effect on virus infections. The invention surprisingly showed that recombinant mistletoe lectins can be effectively used against virus infections, as the examples impressively show. The cytotoxicity of the sequences according to the invention, in particular Aviscumin, is already 0.5 ng/plaque.

Compared to the mistletoe lectins in the related art, the recombinant mistletoe lectins particularly advantageously include no impurities, so that even a lower dosage has increased effectiveness. Moreover, recombinant mistletoe lectins allow high dosage precision to be achieved, whereby successful (locally) specific antiviral treatment is possible.

The antiviral agent according to the invention is therefore used for treating one of the following virus infections: Herpes simplex virus infection, adenovirus infection, poliovirus infection, poxvirus infection, parvovirus infection, papovavirus infection, hepadnavirus infection, orthomyxovirus infection, papilloma virus infection, paramyxovirus infection, coronavirus infection, picornavirus infection, reovirus infection, togavirus infection, flavivirus infection, arenavirus infection, rhabdovirus infection, and retrovirus infection.

The invention further relates to the treatment of skin virus warts, anogential warts, mucous membrane warts and malignant tumors such as cervical cancer, penis and vulvar cancer, in particular as part of a papilloma virus infection (HPV).

The invention also relates to a medicinal drug for treating virus infections, comprising the recombinant mistletoe lectin polypeptide, optionally together with a pharmaceutically compatible carrier. Examples of particularly suitable pharmacologically compatible carriers are known to a person skilled in the art and include buffered salt solutions, water, emulsions such as oil/water emulsions, different types of detergents, sterile solutions, and the like. Medicinal drugs that include such carriers can be formulated by way of known conventional methods. These medicinal drugs can be administered to an individual in a suitable dosage. The administration can take place locally, orally or parenterally, for example, intravenously, intraperitoneally, subcutaneously, intramuscularly, locally, intranasally, intrabronchially or intradermally, or via a catheter in a location of an artery. The type of dosage is determined by the treating physician based on the clinical factors. It is known to a person skilled in the art that the type of dosage is dependent on various factors, for example the body size or the weight, the body surface, the age, the gender or the general state of health of the patient, but also the agent to be specifically administered, the duration and type of administration, and other medicinal drugs that may be administered at the same time.

The invention further relates to a pharmaceutical composition, comprising the recombinant mistletoe lectin polypeptides according to the invention. The composition can be administered locally or systemically. Preparations for a parenteral administration include sterile aqueous or non-aqueous solutions, suspensions and emulsions. Examples of non-aqueous solutions include propylene glycol, polyethylene glycol, vegetable oils such as olive oil, and organic ester compounds such as ethyl oleate, which are suitable for injections. Aqueous carriers include water, alcoholic aqueous solutions, emulsions, suspensions, salt solutions and buffered media. Parenteral carriers include sodium chloride solutions, Ringer's dextrose, dextrose, and sodium chloride, Ringer's lactate and bound oils. Intravenous carriers include, for example, liquid, nutrient and electrolyte supplements (such as those based on Ringer's dextrose).

The composition according to the invention can also include preservatives and other additives, such as antimicrobial compounds, antioxidants and complexing agents. Moreover, compounds such as interleukins, interferons or a non-specific immune modulatory agent may be present. Cytostatic agents, antibiotics and combinations thereof may likewise be present.

According to the invention, the pharmaceutical composition is used for treating the virus infections described above.

The composition according to the invention is preferably present as a solution, gel or cream.

The invention further relates to the use of a recombinant mistletoe lectin for producing an antiviral agent for treating said virus infections. The treatment preferably comprises the administration of a therapeutically effective quantity of the recombinant mistletoe lectin to a person who has contracted, or is expected to contract, an infection.

The effectiveness of the invention for treating virus infections will be described based on the following analysis by way of example.

The following examples are provided to describe the invention, without limiting the invention to these examples.

EXAMPLES

Vero cells (renal cells from African green monkeys) and BGM cells (renal cells from Borgio green monkeys) were incubated for 2 hours with Herpes simplex viruses type 1 (HSV-1) as part of a $\log_{10}$ dilution series. The virus was removed after the cells were infected. The recombinant mistletoe lectin was diluted with cell culture medium, which was used both with and without interfering substances. The interfering substances used were 10% fetal calf serum (FCS) and 3% bovine serum albumin with sheep erythrocytes. 200 μl of the solution with recombinant mistletoe lectin was applied per well to the infected cells. Cell culture medium was applied to the infected cells for virus control purposes. Aciclovir (1.5 mmol) was used in place of the recombinant mistletoe lectin as a negative control substance against HSV-1. The cells were incubated at 37° C.+/−1° C. for 2 to 7 days.

After incubation, the cells were analyzed for cytopathic effects (CPE) using an inverted microscope, and the 50% infectious dose, based on a cell culture, $TCID_{50}$/ml (tissue culture infectious dose) was determined. If no cytopathic effects were visible, this meant that the viruses had been successfully inactivated by the recombinant mistletoe lectin.

So as to gain a more detailed impression of the virus reduction, a plaque reduction assay was conducted, so as to determine the antiviral effectiveness of the recombinant mistletoe lectin. For this purpose, the Vero cells/BGM cells were placed in 12-well plates.

The semi-adherent cells were incubated for 2 hours with a $\log_{10}$ dilution series of the HSV-1 (100 μl per well). The virus was removed after the cells were infected. The recombinant mistletoe lectin was diluted with cell culture medium (with and without interfering substances) and mixed 1:1 with warm agarose. The interfering substances used were fetal calf serum and sheep erythrocytes.

2 ml of the solution comprising the recombinant mistletoe lectin was applied to the infected cells. Cell culture medium was applied to the infected cells for virus control purposes. Aciclovir (1.5 mmol) was used in place of the recombinant mistletoe lectin as a negative control substance against HSV-1. After gelling of the agarose, the cells were incubated at 37° C.+/−1° C. for 7 days. After the incubation period, the cells were fixed for 4 hours with methanol comprising 4% sodium chloride. The cells were then dyed with crystal violet. The virus-induced plaque was counted under the microscope and the $TCID_{50}$/ml was determined.

The following validation steps were conducted as part of this analysis:

- identification of the suitable virus titer with the corresponding cell line;
- identification of the concentration of recombinant mistletoe lectin that is tolerated by the corresponding cell line by measurement of the cytotoxicity and vitality;
- identification of the concentration of recombinant mistletoe lectin that leaves the cell line vulnerable to a virus infection.

Results:

The analysis surprisingly showed an antiviral effectiveness of recombinant mistletoe lectin against HSV-1 and against adenovirus type 5. In the suspension assay with HSV-1/BGM cells, a concentration of 50 ng/ml of recombinant mistletoe lectin caused a virus titer reduction of 2.43 $\log_{10}$ without interfering substances and without the use of MicroSpin columns (see Table 2). A concentration of 500 ng/ml of recombinant mistletoe lectin produced a virus titer reduction of 2.57 $\log_{10}$ and ≥3.29 $\log_{10}$ when using MicroSpin columns and FCS as the interfering substance (see Table 2).

In the plaque reduction assay, an average relative inhibition of the HSV-1 infection of 17.04% was shown at a concentration of 0.5 ng/ml of recombinant mistletoe lectin (without MicroSpin filtration), and an average relative inhibition of the HSV-1 infection of 7.41% was shown with MicroSpin filtration (see Table 3).

The average relative inhibition of the adenovirus type 5 infection in the plaque reduction assay was 79.7% at a concentration of 0.5 ng/ml recombinant mistletoe lectin (without MicroSpin filtration), and 22.2% with MicroSpin filtration (see Table 4).

TABLE 1

Results of the cytotoxicity tests of the test cells

| Cell Line | Vero with MicroSpin | Vero without MicroSpin | BGM with MicroSpin 7 days incubation | BGM without MicroSpin 7 days incubation |
|---|---|---|---|---|
| Recombinant mistletoe lectin 5000 ng/ml | cytotoxic | cytotoxic | n.t. | n.t. |
| Recombinant mistletoe lectin 500 ng/ml | cytotoxic | cytotoxic | cytotoxic | cytotoxic |
| Recombinant mistletoe lectin 50 ng/ml | cytotoxic | cytotoxic | negative | negative |
| Recombinant mistletoe lectin 5 ng/ml | negative | cytotoxic | negative | negative |
| Recombinant mistletoe lectin 0.5 ng/ml | negative | negative | negative | negative |
| Recombinant mistletoe lectin 0.05 ng/ml | negative | negative | negative | negative |
| Recombinant mistletoe lectin 0.005 ng/ml | n.t. | n.t. | negative | negative |
| Negative control substance | n.t. | negative | n.t. | negative | n.t. = not tested

TABLE 2

Test for antiviral effectiveness of recombinant mistletoe lectin with HSV-1, host BGM cells (cell suspension)

| | | HSV-1 Virus (TCID$_{50}$/ml) | Virus titer reduction ($\log_{10}$) + 95% conf. limits |
|---|---|---|---|
| Virus control | | $10^{-6.64+/-0.46}$ | — |
| | | $10^{-6.93+/-0.36}$ | |
| Recombinant mistletoe lectin 5 ng/ml | oSS, without MicroSpin | $10^{-6.79+/-0.36}$ | no virus titer reduction |
| | oSS, with MicroSpin | $10^{-6.79+/-0.36}$ | no virus titer reduction |
| | FCS, without MicroSpin | $10^{-6.79+/-0.54}$ | no virus titer reduction |
| | FCS, with MicroSpin | $10^{-6.64+/-0.46}$ | no virus titer reduction |
| Recombinant mistletoe lectin 50 ng/ml | oSS, without MicroSpin | $10^{-4.21+/-0.54}$ | 2.43 +/− 0.71 |
| | oSS, with MicroSpin | $10^{-6.36+/-0.56}$ | 0.28 +/− 0.72 |
| | FCS, without MicroSpin | $10^{-6.36+/-0.54}$ | 0.28 +/− 0.65 |
| | FCS, with MicroSpin | $10^{-6.36+/-0.46}$ | 0.28 +/− 0.65 |
| Recombinant mistletoe lectin 500 ng/ml | FCS, with MicroSpin | $10^{-4.07+/-0.49}$ | 2.57 +/− 0.67 |
| | | ≤$10^{-3.64+/-0.28}$ | ≥3.29 +/− 0.54 | oSS = without interfering substances

TABLE 3

Test for antiviral effectiveness of recombinant mistletoe lectin, plaque assay with HSV-1 on Vero cells

| | | | | Recombinant mistletoe lectin | | |
|---|---|---|---|---|---|---|
| Virus dilution | | Virus control | Aciclovir (1.5 mmol) | 0.5 ng/ml without Spin | 0.5 ng/ml with Spin | 0.5 ng/ml with Spin |
| $10^{-5.0}$ | Number of plaque | >50, >50, 6 | 0, 0, 0 | >50, >50, >50 | 10, >50, >50 | cytotoxic |
| | Mean value | >35 | 0 | >50 | >36 | |
| | StabW | n.d. | 0 | n.d. | n.d. | n.d. |
| | Relative infectiosity | 100 | 0 | 100 | 100 | n.d. |
| | Relative inhibition | 0 | 100 | 0 | 0 | n.d. |
| $10^{-5.48}$ | Number of plaque | 5, 5, 4, 4 | 0, 0, 0, 0 | 6, 5, 3, 2 | 3, 4, 4, 3 | cytotoxic |
| | Mean value | 4.5 | 0 | 4.0 | 3.5 | |
| | StabW | 0.57 | 0 | 1.82 | 0.57 | n.d. |
| | Relative infectiosity | 100 | 0 | 88.88 | 77.77 | n.d. |
| | Relative inhibition | 0 | 100 | 11.12 | 22.23 | n.d. |
| | Number of plaque | 2, 3, 3, 2 | 0, 0, 0, 0 | 1, 2, 1, 2 | 2, 3, 1, 4 | cytotoxic |
| | Mean value | 2.5 | 0 | 1.5 | 2.5 | |
| $10^{-5.95}$ | StabW | 0.57 | 0 | 0.57 | 1.29 | n.d. |

TABLE 3-continued

Test for antiviral effectiveness of recombinant mistletoe lectin, plaque assay with HSV-1 on Vero cells

| Virus dilution | | Virus control | Aciclovir (1.5 mmol) | Recombinant mistletoe lectin | | |
|---|---|---|---|---|---|---|
| | | | | 0.5 ng/ml without Spin | 0.5 ng/ml with Spin | 0.5 ng/ml with Spin |
| | Relative infectiosity | 100 | 0 | 60.0 | 100 | n.d. |
| | Relative inhibition | 0 | 100 | 40.0 | 0 | n.d. |
| Average | relative inhibition | n.a. | 100 | 17.04 | 7.41 | n.d. | n.d. = not detectable
n.a. = not to be evaluated

TABLE 4

Test for antiviral effectiveness of recombinant mistletoe lectin, plaque assay with adenovirus type 5 on BGM cells

| Virus dilution | | Virus control | Recombinant mistletoe lectin | | |
|---|---|---|---|---|---|
| | | | 0.5 ng/ml without Spin | 0.5 ng/ml with Spin | 0.5 ng/ml with Spin |
| $10^{-4.0}$ | Number of plaque | 5, 5, 8 | 2, 3, 0 | 11, 8, 8 | cytotoxic |
| | Mean value | 6 | 1.66 | 9 | |
| | StabW | 1.7 | 1.52 | 1.73 | n.d. |
| | Relative infectiosity | 100 | 27.7 | 100 | n.d. |
| | Relative inhibition | 0 | 72.3 | 0 | n.d. |
| $10^{-4.46}$ | Number of plaque | 3, 4, 2, 3 | 0, 0, 0, 0 | 4, 2, 2, 4 | cytotoxic |
| | Mean value | 3 | 0 | 3 | |
| | StabW | 0.81 | 0 | 1.15 | n.d. |
| | Relative infectiosity | 100 | 0 | 100 | n.d. |
| | Relative inhibition | 0 | 100 | 0 | n.d. |
| $10^{-4.95}$ | Number of plaque | 1, 1, 2, 2 | 0, 0, 2, 0 | 0, 0, 0, 2 | cytotoxic |
| | Mean value | 1.5 | 0.5 | 0.5 | |
| | StabW | 0.57 | 1.0 | 1.0 | n.d. |
| | Relative infectiosity | 100 | 33.3 | 33.3 | n.d. |
| | Relative inhibition | 0 | 66.7 | 66.7 | n.d. |
| Average relative inhibition | | n.a. | 79.7 | 22.2 | n.d. | n.d. = not detectable
n.a. = not to be evaluated

The invention claim is:

1. A method of treating a viral infection comprising administering to a patient with a viral infection a drug containing a recombinant mistletoe lectin, wherein the recombinant mistletoe lectin is a mistletoe lectin A-chain selected from the group consisting of the amino acid sequences of SEQ ID NO: 1-3, or comprises parts and fragments thereof, or is a combination thereof, and wherein the viral infection comprises Herpes simplex virus infection.

2. The method of claim 1, wherein a cytotoxicity of recombinant mistletoe lectin is less than 0.5 ng/plaque.

3. The method of claim 1, wherein the drug further comprises a pharmaceutically acceptable carrier.

4. The method of claim 1, wherein the drug further comprises interleukins, interferons, a cytostatic agent.

5. The method according to claim 1, wherein the recombinant mistletoe lectin further comprises a mistletoe lectin B-chain selected from the group consisting of amino acid sequences of SEQ ID NOs: 4-12, or comprises parts and fragments thereof, or is a combination thereof.

6. The method according to claim 1, wherein the recombinant mistletoe lectin further comprises a mistletoe lectin A-chain of amino acid sequence of SEQ ID NO: 1 and further comprises the mistletoe lectin B-chain of amino acid sequence SEQ ID NO: 4.

7. A method of reducing a recurrence of a viral infection comprising administering to a patient with a viral infection a drug containing a recombinant mistletoe lectin, wherein the recombinant mistletoe lectin is a mistletoe lectin A-chain selected from the group consisting of the amino acid sequences of SEQ ID NOs: 1-3, or comprises parts and fragments thereof, or is a combination thereof, wherein the viral infection comprises Herpes simplex virus infection.

8. The method according to claim 7, wherein the recombinant mistletoe lectin further comprises a mistletoe lectin B-chain selected from the group consisting of amino acid sequences of SEQ ID NOs: 4-12, or comprises parts and fragments thereof, or is a combination thereof.

* * * * *